United States Patent [19]

Burstein

[11] Patent Number: 5,178,856
[45] Date of Patent: * Jan. 12, 1993

[54] ENHANCING GROWTH OF MEGAKARYOCYTES IN MAMMALS USING INTERLEUKIN 6

[75] Inventor: Samuel A. Burstein, Edmond, Okla.

[73] Assignee: Board of Regents of the University of Oklahoma, Norman, Okla.

[*] Notice: The portion of the term of this patent subsequent to Feb. 11, 2009 has been disclaimed.

[21] Appl. No.: 700,661

[22] Filed: May 15, 1991

Related U.S. Application Data

[63] Continuation of Ser. No. 306,479, Feb. 2, 1989, Pat. No. 5,087,448.

[51] Int. Cl.$^5$ .............................................. A61K 45/05
[52] U.S. Cl. .................................... 424/85.2; 424/85.1
[58] Field of Search ............................... 424/85.1, 85.2

[56] References Cited

PUBLICATIONS

Ikebuchi et al., "Interleukin 6 Enhancement of Interleukin 3-Dependent Proliferation of Multipotential Hemopoietic Progenitors" Proc. Natl. Acad. Sci., vol. 84, p. 9035-9039, Dec. 1987.

*Primary Examiner*—Lester L. Lee
*Assistant Examiner*—Choon Koh
*Attorney, Agent, or Firm*—Dunlap, Codding & Lee

[57] ABSTRACT

A therapeutic method for treating mammals by administering an effective dosage of a substance comprising interleukin 6 and interleukin 3 into the mammal for enhancing the growth of megakaryocytes and platelets.

13 Claims, 3 Drawing Sheets

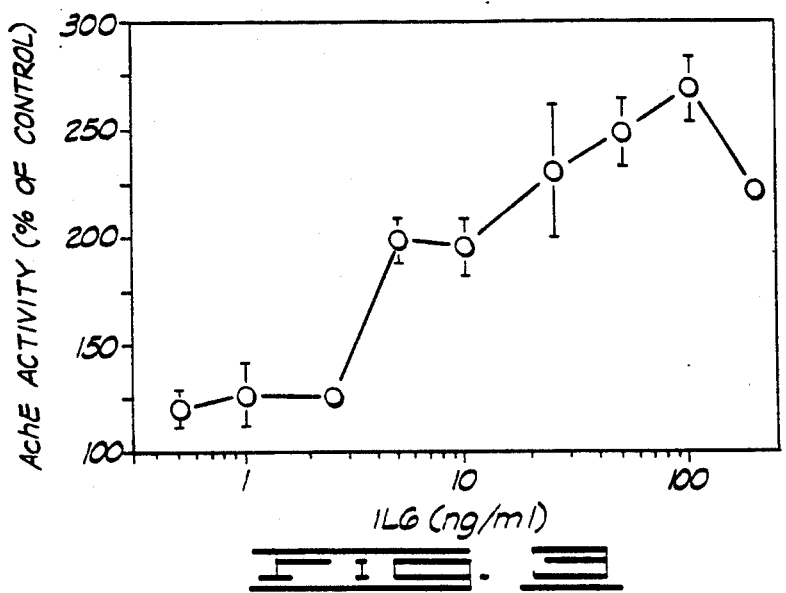
FIG. 3
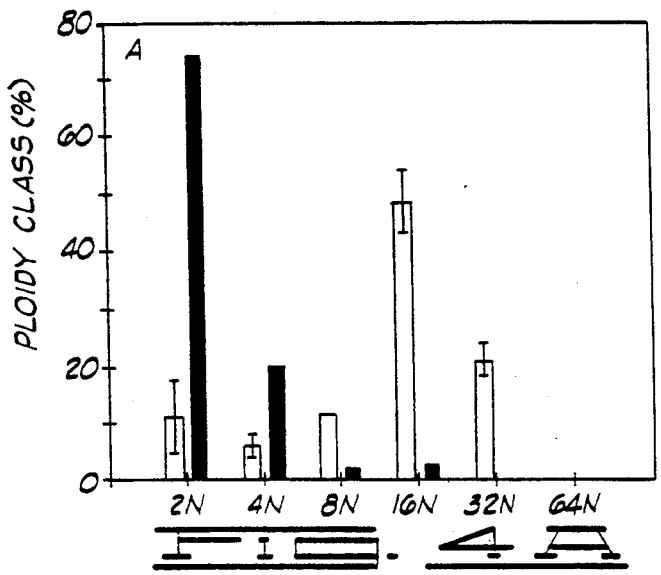
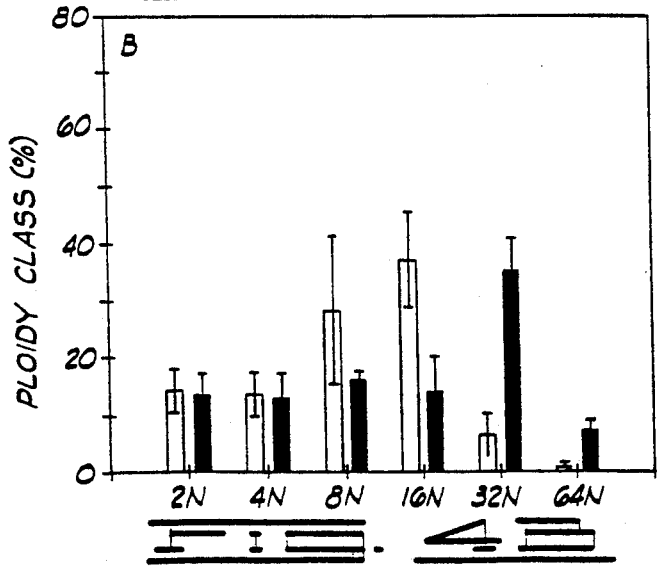

ENHANCING GROWTH OF MEGAKARYOCYTES IN MAMMALS USING INTERLEUKIN 6

This is a continuation of co-pending application Ser. No. 306,479 filed on Feb. 2, 1989, now U.S. Pat. No. 5,087,448, issued Feb. 11, 1992.

FIELD OF THE INVENTION

The present invention relates to treating a mammal such as a human in need of such therapy with a substance comprising interleukin 6 (IL6) or interleukin 6 and interleukin 3 for enhancing the growth of the megakaryocytes.

BRIEF DESCRIPTION OF THE DRAWINGS

FIG. 3 is a graph of cultured cells showing increased AchE concentration in response to IL6.

FIG. 4a is a graph showing the ploidy of normal megakaryocytes: unfilled square shows directly from marrow; and filled square shows following establishment in culture.

FIG. 4b is a graph showing the ploidy of megakaryocytes cultured with IL6: unfilled square shows control; and filled square shows IL6.

BRIEF DESCRIPTION OF THE PREFERRED EMBODIMENTS

Figure 1A:
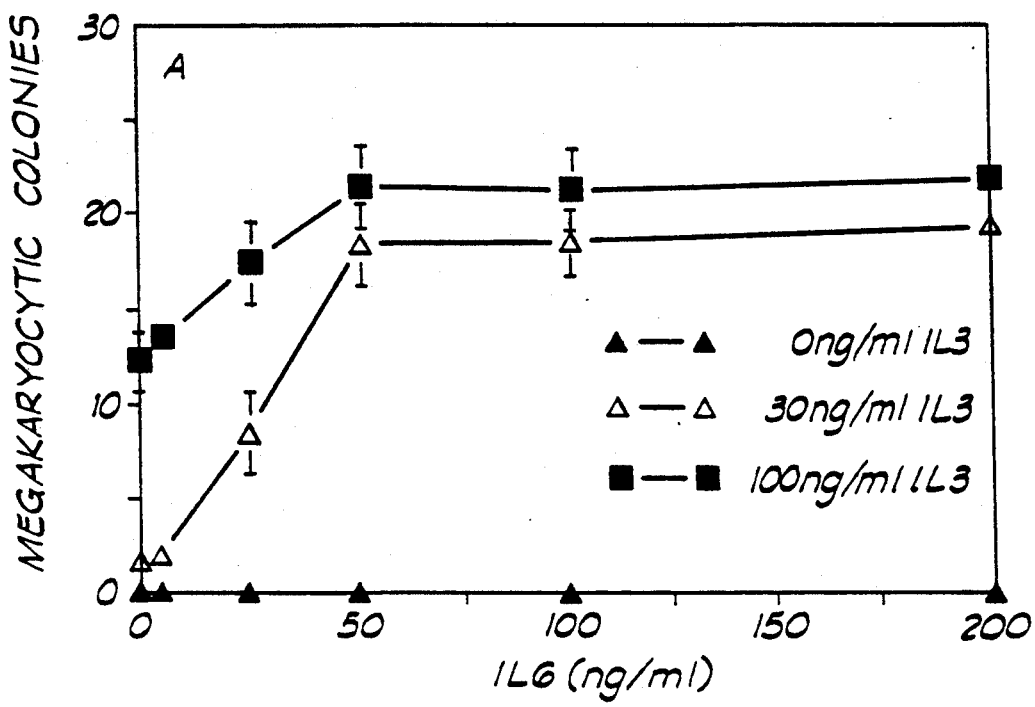
FIG. 1 is a graph showing the influence of varying concentrations of added IL6 on the appearance of megakaryocytic (A) and granulocyte-macrophage (GM) (B) colonies.

The blood platelets are minute circulating cells that, among many important functions, are crucial for the prevention of bleeding, and for the cessation of bleeding once it has begun. The blood platelets are derived from bone marrow cells designated megakaryocytes. Megakaryocytes are unable to divide, but mature by an unusual process whereby they progressively increase in size. The platelets, via unknown mechanisms, are then shed from the cytoplasm of the megakaryocytes. Over the past several years, a number of proteins (designated growth factors) have been described that regulate the development of other bone marrow cells that give rise to red cells and various types of white cells; however, no factor has been described that directly and potently induces megakaryocyte maturation. Several of these growth factors, including erythropoietin, granulocyte-macrophage colony stimulating factor, granulocyte colony stimulating factor, and interleukin 3 have been shown to raise various blood cell counts in man.

The present invention comprises a method for treating a mammal in need of such therapy with recombinant human growth factor designated interleukin 6 (IL6) which is a factor involved in the growth of certain types of lymphocytes, liver cells, and very primitive bone marrow precursor cells. IL6 is a potent megakaryocyte growth promotor.

Presently patients with low platelet counts must receive platelet transfusions with the attendant hazards of blood transfusion. Despite adequate responses to platelet transfusions in many patients, many others become refractory to them for immunologic reasons and no longer get an increment in the platelet count following transfusion. A significant morbidity and mortality is observed in such patients. IL6 endogenously raises the platelet count without platelet transfusion and is therefore useful in hastening the recovery of the platelet count in those patients whose megakaryocytes have been suppressed by chemotherapy or radiotherapy for malignant diseases. IL6 also enhances platelet recovery in patients following bone marrow transplantation and is useful for the in vitro production of platelets.

The response of cells of the murine megakaryocytic lineage to human interleukin 6 (IL6), a multi-functional growth factor, was assessed in serum-free cultures using a variety of biological assays. IL6 had no influence on megakaryocytic colony formation but augmented the numbers of colonies promoted by interleukin 3. However, in liquid marrow cultures IL6 alone promote marked increments in megakaryocytic size and total acetylcholinesterase (AchE) content. Moreover, the factor induced a significant shift toward higher ploidy classes when megakaryocytic DNA was quantitated by flow cytometry. To determine if the influence of IL6 on megakaryocytic maturation was direct, the factor was added to cultures of single megakaryocytes isolated from megakaryocytic colonies. Fifty-four percent of these cells increased in size compared to 19% of those grown without IL6. The data show that human IL6 is a potent direct-acting growth factor for murine megakaryocytes with activity restricted to maturation of that lineage.

Megakaryocyte growth can be functionally divided into two phases: a stage of proliferation of megakaryocytic precursor cells and their mitotic progeny; and a stage of cellular maturation, encompassing nuclear endoreduplication (polyploidization), cytoplasmic enlargement and acquisition of platelet antigens. Studies in experimental animals have suggested that each of these phases is independently regulated. The multipotent colony stimulating factor interleukin 3, granulocyte-macrophage (GM) colony stimulating factor and erythropoietin have been shown to promote the proliferation of megakaryocytic progenitors. However, these growth factors have the capacity to support not only proliferation, but also megakaryocytic maturation. These observations, nonetheless, do not exclude the notion that there exists growth factors whose actions are restricted to either the proliferative or maturational phase.

Recombinant human interleukin 6 is a 26,000 $M_r$ glycoprotein with multiple biological activities, has been purified to homogeneity from both murine and human sources, and recently has been molecularly cloned. This cytokine has a remarkable influence on megakaryocytic maturation, but virtually none on proliferation.

MATERIALS AND METHODS

Marrow Preparation. Marrow was flushed from the femurs of $C_{57}Bl/6$ mice with Iscove's modification of Dulbecco's medium (IMDM) supplemented with Nutridoma-SP (Boehringer Mannheim, Indianapolis, Ind.), a serum-free medium supplement. For culture studies, a single cell suspension was made by repetitive expulsion through progressively smaller needles. For flow cytometry controls, a monocellular suspension was made by gentle filtration through a 100 μm nylon mesh. In some experiments, marrow cells were treated with 0.5 mM diisopropylfluorophosphate to inactivate endogenous AchE In other experiments, adherent cells were removed to enrich the numbers of megakaryocytes or their progenitor cells. Up to $2 \times 10^6$ cells/ml were incubated in the presence of 10% horse serum in IMDM for 45 min at 37° C. in plastic tissue culture flasks, followed by repetitive washing in IMDM to remove the serum.

Colony Assays. To determine the influence of IL6 on colony formation with or without the presence of the multipotential colony stimulating factor IL3, megakaryocytic and GM colony assays were performed in a serum-free system. $10^5$ nonadherent marrow cells were cultured in 35 mm tissue culture dishes using IMDM supplemented with 1% bovine serum albumin (BSA), 360 μg/ml human transferrin, 0.98 μg/ml cholesterol and made semi-solid with 0.3% agar. Following 7 days in culture at 37° C., the agar discs were transferred to glass slides and fixed with 2% glutaraldehyde. Colonies were enumerated following histochemical staining for AchE (a marker enzyme of megakaryocytes in murine marrow) and counterstaining with hematoxylin.

Liquid Cultures. Liquid marrow cultures were performed in serum-free conditions as described previously. $10^5$ nucleated non-adherent marrow cells were set up in 96 well culture plates in 0.2 ml IMDM supplemented with 1% Nutridoma in the presence of varying concentrations of growth factors. The plates were incubated at 37° C. for 4-5 days. The numbers and size of megakaryocytes was assessed following histochemical staining for AchE. AchE activity was measured using a modification of our previously reported fluorometric method. See Ishibashi, T., Kozoil, J. A. & Burstein, S. A. (1987) J. Clin. Invest. 79, 286-289. One hundred eighty μl of a solution of 0.2% Triton X-100 in 1 mM EDTA, 0.12M NaCl, and 50 mM Hepes, pH 7.5 was added to each well, followed by the addition of 20 μl acetylthiocholine iodide (final concentration 0.56 mM). Following 3 hrs incubation at room temperature, 20 μl of the reaction mixture from each well was transferred to the corresponding wells of a 96-well Microfluor "B" plate (Dynatech Laboratories, Alexandria, Va.). Twenty μl of 0.4 mM coumarinphenylmaleimide (Molecular Probes, Junction City,Oreg.) was then added followed by 160 μl of diluent buffer consisting of 0.2% Triton X-100, 50 mM Na acetate, 1 mM EDTA pH 5.0. The fluorescence emission was determined on a fluorometer capable of reading 96-well plates (Multifluor, Dynatech), interfaced with an IBM PC-AT compatible computer. The DNA content of megakaryocytes grown in liquid culture was assessed by flow cytometry, using a modification of our previously described technique. See Tomer, A., Harker, L. A. & Burstein, S. A. (1987) Blood 70, 1735- and Tomer, A., Harker, L. A. & Burstein, S. A. (1988) Blood 71, 1244-1252. Following 5 days in culture, the contents of 4 replicate wells were incubated for 30 min at 4° C. with a saturating concentration of fluoresceinated rabbit anti-mouse platelet globulin. The antiserum was prepared as described previously, and was extensively absorbed with mouse red cells and platelet-poor buffy coat. The serum was treated by precipitating twice with 50% $(NH_4)_2SO_4$, and fluoresceinated to an F/P ratio of 2.2:1 by standard techniques. Controls were incubated identically with fluoresceinated rabbit IgG. Following immunofluorescent labelling, the cells were stained with propidium iodide to assess DNA content. Cells were analyzed with a Coulter Epics V flow cytometer using a 100 μm diameter nozzle. Megakaryocytes were selected on the basis of membrane immunofluorescence by setting an electronic gate at a fluorescence level above that of the antibody control. The ploidy distribution was determined by setting markers at the nadirs between peaks using the 2N and 4N peaks of the cells as an internal standard.

Single Cell Cultures. To determine if the influence of IL6 was direct, isolated single megakaryocytes were set up in liquid culture as described previously. Marrow was enriched for progenitor cells on a 1.065/1.077 g/cm$^3$ discontinuous Percoll gradient and cultured in methylcellulose for 5 days until megakaryocytic colonies were recognizable in situ. Individual colonies were removed under an inverted microscope with a micropipette in 2 μl volumes and dispersed in 2 ml IMDM. Individual megakaryocytes were removed in 1 μl volumes and recultured for 24-36 hrs in 35 μl of IMDM containing 3% BSA, 1% Nutridoma, 50 μM 2-mercaptoethanol and 0 or 200 ng/ml IL6 in microwell plate covers. Cell diameter was measured at the outset and completion of culture.

Growth Factors. Murine recombinant IL3 was purchased from Genzyme (Boston, Mass.). Recombinant human IL6 was expressed in *E. coli* and was purchased from R&D Systems (Minneapolis, Minn.).

RESULTS

Figure 1B:
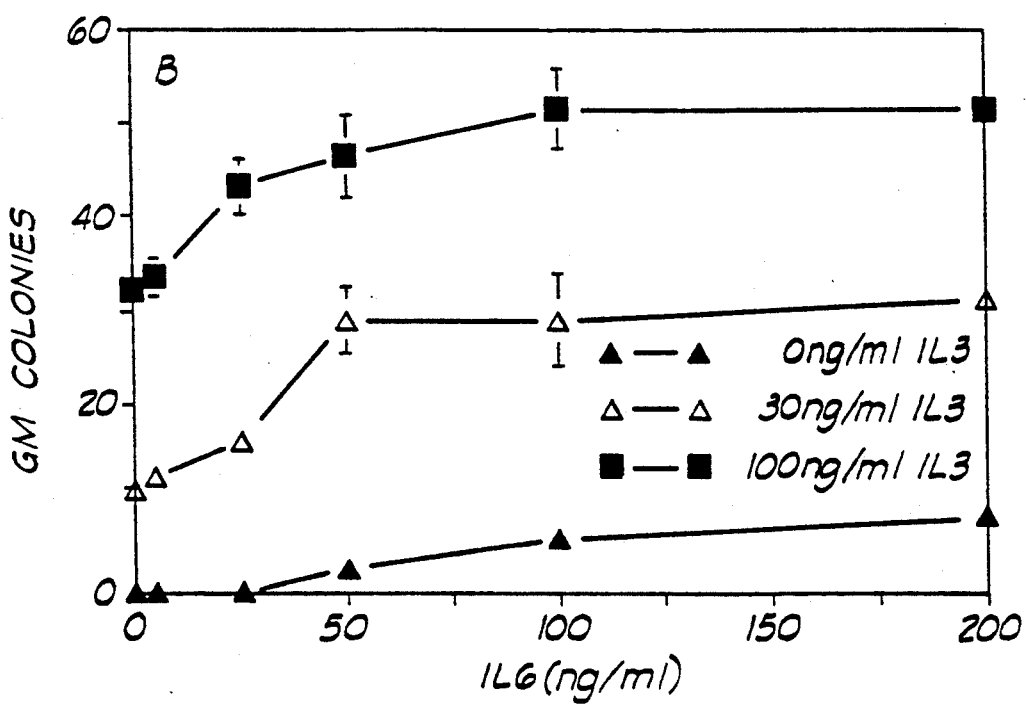

Effect of IL6 on Colony Formation. FIG. 1 shows the influence of varying concentrations of added IL6 on the appearance of megakaryocytic and GM colonies. When added alone in concentrations up to 200 ng/ml, IL6 did not promote megakaryocytic colony formation. However, the factor augmented the numbers of megakaryocytic colonies enumerable in the presence of suboptimal (30 U/ml) and optimal (100 U/ml) concentrations of IL3 (a dose-response analysis with IL3 alone showed that concentrations of IL3 ≧100 U/ml induced maximal colony formation). A small number of GM colonies was first noted with 50 ng/ml IL6 alone. At an IL6 concentration of ≧25 ng/ml, a significant increment in GM colonies was observed with 30 U/ml IL3, compared to no added IL6 (p<0.05). Similarly, IL6 augmented GM colony formation in the presence of 100 U/ml IL3.

The foregoing shows that IL6 is not only specific for maturation (at least in the megakaryocytic lineage), but also is a more potent maturation inducer than IL3. Consequently, IL6 alone would have no effect on colony formation; rather, the factor would permit detection of a proportion of immature unrecognizable megakaryocytic colonies developing in response to IL3. To study the effects of IL6 on maturation, a liquid culture system was employed to measure the size, AchE content and ploidy of megakaryocytes.

Figures 2A, 2B:
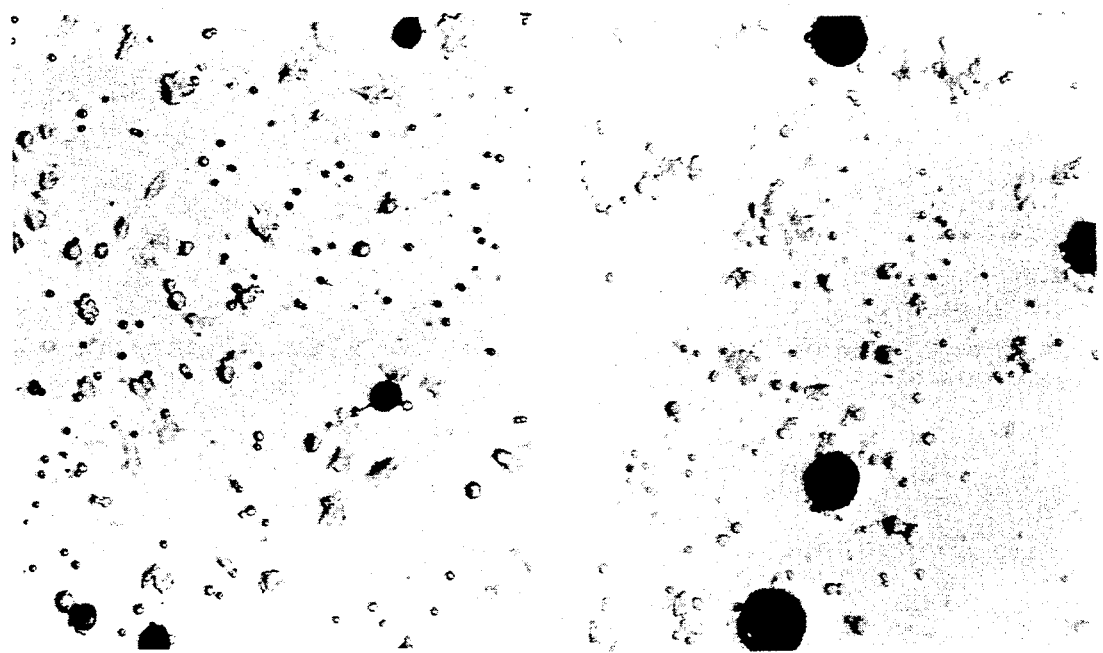
FIG. 2 is a photograph of cultured cells stained for AchE: A—control; B—IL6; C—IL3; and D—IL3 and IL6.
Figure 2C:
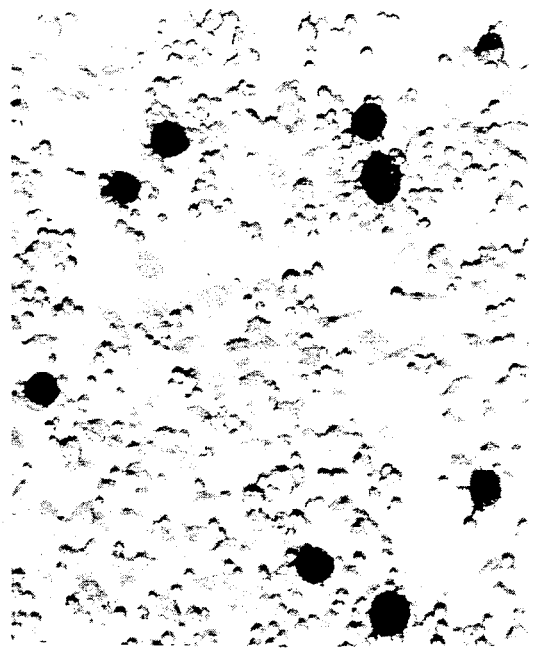
Figure 2D:
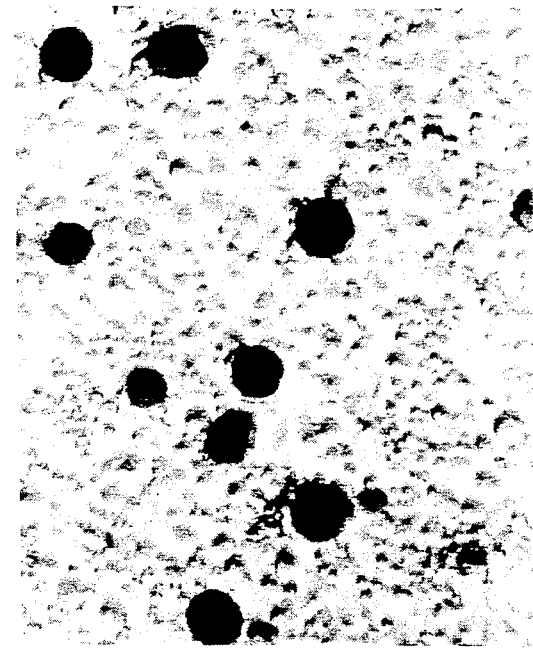

Influence of IL6 on Megakaryocyte Number and Size. When IL6 was added to serumless liquid cultures, individual megakaryocytes could be recognized in situ at day 2 of culture, and appeared to increase in size over the succeeding 3 days. On day 4 of culture, the cells were stained for AchE, followed by enumeration and size measurement (FIG. 2). A small increment in the numbers of AchE-positive cells was observed at ≧100 ng/ml IL6, but the increments were of borderline significance. In contrast, a significant increase in megakaryocytic diameter was observed at ≧1 ng/ml IL6 compared to cells cultured in the absence of the factor (P<0.01; Table 1).

TABLE 1

| | Influence of IL6 on megakaryocyte number and size in liquid culture | |
|---|---|---|
| IL6 (ng/ml) | No. of Mks[1] | Diameter ± 1 SD[2] |
| 0 | 83 ± 5 | 20.4 ± 4.8 (144) |
| 1 | 81 ± 8 | 25.1 ± 8.2 (122)[3] |
| 10 | 95 ± 14 | 25.4 ± 7.5 (143) |
| 50 | 81 ± 10 | 29.8 ± 7.8 (113) |
| 100 | 101 ± 19 | 32.7 ± 7.3 (124) |
| 200 | 104 ± 19 | 34.1 ± 8.5 (112) |

[1]Number of megakaryocytes per $10^5$ marrow cells plated
[2]Geometric mean of 2 perpendicular diameters. The number of cells measured is indicated in parentheses.
[3]At all concentrations of IL6 ≧1 ng, the differences in diameter compared to control was significant ($p < 0.01$).

Effect of IL6 on AchE Production. In contrast to the failure of IL6 alone to promote megakaryocytic colony formation, the factor significantly increased AchE production at all tested concentrations ≧0.5 ng/ml (FIG. 3).

Influence of IL6 on Ploidy. Control normal mouse marrow showed a modal megakaryocytic ploidy of 16N (49%). However, when cells were assayed immediately following establishment in culture, 95% of all cells binding fluoresceinated antiplatelet globulin were 2 and 4N (FIG. 4a). This was expected since expulsion through 25 gauge needles destroys the majority of the larger megakaryocytes. After 5 days in culture, megakaryocytes developing in the presence of IL6 showed a marked increase in ploidy compared to control cultures, with 35% 32N and 7% 64N cells vs. 6% 32N and 1% 64N cells, respectively (FIG. 4b).

Stimulation of Isolated Single Megakaryocytes. Since marrow comprises heterogeneous populations of cells, it is possible that the observed effects of IL6 are mediated indirectly. To determine if the influence of IL6 was direct, isolated single megakaryocytes were set up in serum-free culture. Table 2 shows that the factor markedly enhanced the percentage of cells increasing in size. Although the effect of IL6 was greatest on cells whose initial diameter was <20 μm (67% increased in size compared to 16% of the control cells), 41% of large megakaryocytes >30 μm in diameter increased in size, compared with 20% of cells grown without IL6.

TABLE 2

| Effect of IL6 on the size of single megakaryocytes isolated from CFU-MK-derived colonies | | |
|---|---|---|
| | Number of Cells Increasing in Diameter/Total Cells Measured (%) | |
| Initial Cell Diameter (μm) | −IL6 | +IL6[1] |
| 10–20 | 3/19 (16) | 18/27 (67) |
| 20–30 | 7/34 (21) | 37/64 (58) |
| >30 | 5/25 (20) | 18/44 (41) |

[1]The size of single megakaryocytes was determined prior to and following 24–36 hrs in culture with or without 200 ng/ml IL6. An increase in size was defined as an increment of ≧0.5 μm. The range of size increments was 0.5–10.6 μm for cells cultured with IL6, and 0.5–5.7 μm for control cells. At each of the initial cell diameter classifications listed, the percentage of cells cultured with IL6 increasing in size was significantly greater than controls ($P < 0.01$).

DISCUSSION

These data show that IL6 exerts potent effects on murine megakaryocytic maturation as assessed by increments in size, AchE activity and ploidy, while exhibiting no influence on megakaryocytic colony formation in the absence of IL3. Moreover, the data show that megakaryocytic size is augmented by IL6 directly. Previous studies from our laboratory have shown that size increments in isolated megakaryocytes correspond with increments in ploidy and AchE content. It is likely then, that there are IL6 receptors on these cells.

Promotion of megakaryocytic maturation defines an additional biological activity of this multifunctional cytokine that includes stimulation of B-cell differentiation, thymocyte proliferation, GM colony formation, hepatocyte stimulation and support of hybridoma growth. More recently, the factor has been shown to act synergistically with interleukin 1 and 3 in the proliferation of early hematopoietic progenitor cells, to induce differentiation of murine leukemia cells and to inhibit the growth of human breast carcinoma and leukemia cell lines.

The response of cells of the murine megakaryocytic lineage to human interleukin 6 (IL6), a multi-functional growth factor, was assessed in serum-free cultures using a variety of biological assays. IL6 had no influence on megakaryocytic colony formation, but augmented the numbers of colonies promoted by interleukin 3. However, in liquid marrow cultures, IL6 alone promoted marked increments in megakaryocytic size and total acetylcholinesterase (AchE) content. Moreover, the factor induced a significant shift toward higher ploidy classes when megakaryocytic DNA was quantitated by flow cytometry. To determine if the influence of IL6 on megakaryocytic maturation was direct, the factor was added to cultures of single megakaryocytes isolated from megakaryocytic colonies. Fifty-four percent of these cells increased in size compared to 19% of those frown without IL6. The data show that human IL6 is a potent direct-acting growth factor for murine megakaryocytes with activity restricted to maturation of that lineage.

IL6 and/or IL3 may be parenterally administered into the mammal. Preferably the interleukins, in purified form, are mixed with a pharmaceutically acceptable carrier such as sterile normal saline. An effective amount of IL6 may vary with different mammals, but generally a range of 0.5–1.5 mcg/kg/day is effective for the enhanced growth of megakaryocytes.

The mixture of IL6 and carrier or IL6 alone may be administered parenterally, and preferably intravenously over a period of time. Generally, continuous intravenous administration for an appropriate period of time is preferred. For example, a human subject with bone marrow depression may require two weeks therapy. A mammal treated with chemotherapeutic agents may require several days therapy.

Changes may be made in the construction and operation of the various steps or in the sequence of the steps of the method described herein without departing from the spirit and scope of the inventor as defined in the following claims.

What is claimed is:

1. A method to enhance the growth of and production of platelets from a megakaryocyte in vitro, comprising:
   exposing the megakaryocyte in vitro to an effective amount of a substance comprising interleukin 6.

2. The method of claim 1 in which the interleukin 6 is human interleukin 6.

3. The method of claim 1 in which the substance further comprises interleukin 3.

4. The method of claim 1 in which the substance further comprises interleukin 3 and interleukin 6 administered sequentially.

5. The method of claim 1 in which the substance further comprises interleukin 3 and interleukin 6 administered concurrently.

6. A method of in vitro treatment of both a megakaryocyte progenitor and a megakaryocyte, wherein such treatment increases megakaryocyte numbers and promotes megakaryocyte growth, comprising:
    exposing both the megakaryocyte progenitor and the megakaryocyte in vitro to an effective amount of a substance comprising interleukin 3 and interleukin 6.

7. The method of claim 6 wherein interleukin 3 and interleukin 6 are administered sequentially.

8. The method of claim 6 wherein interleukin 3 and interleukin 6 are administered concurrently.

9. The method of claim 6 in which the interleukin 6 is human interleukin 6.

10. A method of treating both a megakaryocyte progenitor and a megakaryocyte in vitro, comprising:
    exposing both the megakaryocyte progenitor and the megakaryocyte in vitro to an effective amount of a substance comprising interleukin 6, wherein said substance acts in vitro to increase megakaryocyte numbers, promote megakaryocyte growth, and enhance the differentiation of the megakaryocyte into a plateletproducing cell.

11. The method of claim 10 in which the substance further comprises interleukin 3 and interleukin 6, wherein the interleukin 3 and the interleukin 6 are administered sequentially.

12. The method of claim 10 in which the substance further comprises interleukin 3 and interleukin 6, wherein the interleukin 3 and the interleukin 6 are administered concurrently.

13. The method of claim 10 in which the interleukin 6 is human interleukin 6.

* * * * *